United States Patent
Liang et al.

(10) Patent No.: US 10,515,724 B2
(45) Date of Patent: Dec. 24, 2019

(54) METHOD AND SYSTEM FOR DETERMINING AN ASSOCIATION OF BIOLOGICAL FEATURE WITH MEDICAL CONDITION

(71) Applicant: Macau University of Science and Technology, Taipa (MO)

(72) Inventors: Yong Liang, Taipa (MO); Hai-Hui Huang, Taipa (MO); Xiao-Ying Liu, Taipa (MO)

(73) Assignee: MACAU UNIVERSITY OF SCIENCE AND TECHNOLOG, Taipa (MO)

( * ) Notice: Subject to any disclaimer, the term of this patent is extended or adjusted under 35 U.S.C. 154(b) by 670 days.

(21) Appl. No.: 15/150,732

(22) Filed: May 10, 2016

(65) Prior Publication Data
US 2017/0329913 A1    Nov. 16, 2017

(51) Int. Cl.
*G06N 7/02*    (2006.01)
*G16H 50/20*   (2018.01)

(52) U.S. Cl.
CPC ............. *G16H 50/20* (2018.01); *G06N 7/023* (2013.01)

(58) Field of Classification Search
None
See application file for complete search history.

(56) References Cited

PUBLICATIONS

"Sparse logistic regression with a L1/2 penalty for gene selection in cancer classification," Yong Liang, Cheng Liu, Xin-Ze Luan, Kwong-Sak Leung, Tak-Ming Chan, Zong-Ben Xu, and Hai Zhang, BMC Bioinformatics 2013, 14:198 (Year: 2013).*
Application of L1/2 regularization logistic method in heart disease diagnosis, Bowen Zhang, Hua Chai, Ziyi Yang, Yong Liang, Gejin Chu, and Xiaoying Liu, Bio-Medical Materials and Engineering 24 (2014) 3447-3454 (Year: 2014).*
Generalized Regression Neural Network and Radial Basis Function for Heart Disease Diagnosis, Shaikh Abdul Hannan, R.R. Manza, R.J. Ramteke, International Journal of Computer Applications (0975-8887), vol. 7—No. 13, Oct. 2010 (Year: 2010).*
Accili, D., Arden, K.C. (2004) FoxOs at the Crossroads of Cellular Metabolism, Differentiation, and Transformation. Cell. 117, pp. 421-426.
Beer, D. G., Kardia, S. L., Huang, C., Giordano, T. J., Levin, A. M., Misek, D. E., Lin, L., Chen, G., Gharib, T. G. and Thomas, D. G. (2002) Gene-expression profiles predict survival of patients with lung adenocarcinoma. Nat. Med. 8, pp. 816-824.
Benson, M., Carlsson, L., Guillot, G., Jernås, M., Langston, M., Rudemo, M. and Andersson, B. (2006) A network-based analysis of allergen-challenged CD4+ T cells from patients with allergic rhinitis. Genes Immun. 7, pp. 514-521.

(Continued)

*Primary Examiner* — Hal Schnee
(74) *Attorney, Agent, or Firm* — Renner Kenner Greive Bobak Taylor & Weber

(57) ABSTRACT

A method and a system for determining an association of at least one biological feature with a medical condition utilizes the novel $L_{1/2}$ penalized network-constraint regression model to achieve an improved biological analysis, in particular by solving high-dimensional problems. The method and the system of the present invention attain high accuracy and preciseness.

14 Claims, 5 Drawing Sheets

(56) References Cited

PUBLICATIONS

Breheny, P. and Huang, J. (2011) Coordinate descent algorithms for nonconvex penalized regression, with applications to biological feature selection. Ann. Appl. Stat. 5, 232-253. doi:10.1214/10-AOAS388.

Bullinger, L., Döhner, K., Bair, E., Fröhling, S., Schlenk, R. F., Tibshirani, R., Döhner, H. and Pollack, J. R. (2004) Use of gene-expression profiling to identify prognostic subclasses in adult acute myeloid leukemia. N. Engl. J. Med. 350, pp. 1605-1616.

Calvano, S. E., Xiao, W., Richards, D. R., Felciano, R. M., Baker, H. V., Cho, R. J., Chen, R. O., Brownstein, B. H., Cobb, J. P. and Tschoeke, S. K. (2005) A network-based analysis of systemic inflammation in humans. Nature. 437, pp. 1032-1037.

Chan, A. Y., Coniglio, S. J., Chuang, Y., Michaelson, D., Knaus, U. G., Philips, M. R. and Symons, M. (2005) Roles of the Rac1 and Rac3 GTPases in human tumor cell invasion. Oncogene. 24, pp. 7821-7829.

Chuang, H., Lee, E., Liu, Y., Lee, D. and Ideker, T. (2007) Network-based classification of breast cancer metastasis. Molecular systems biology, p. 3.

Donoghue, D. (2012) ErbB4: A novel therapeutic target in glioblastoma multiforme. Proceedings of the 103rd Annual Meeting of the American Association for Cancer Research, p. 1220.

Dudoit, S., Fridlyand, J. and Speed, T. P. (2002) Comparison of discrimination methods for the classification of tumors using gene expression data. Journal of the American statistical association. 97, pp. 77-87.

Friedman, J., Hastie, T. and Tibshirani, R. (2010) Regularization paths for generalized linear models via coordinate descent. J. Stat. Softw. 33, pp. 1-22.

Golub, T. R., Slonim, D. K., Tamayo, P., Huard, C., Gaasenbeek, M., Mesirov, J. P., Coller, H., Loh, M. L., Downing, J. R., Caligiuri, M. A., Bloomfield, C. D. and Lander, E. S. (1999) Molecular classification of cancer: Class discovery and class prediction by gene expression monitoring. Science. 286, pp. 531-537.

Gomes, A. L., Reis-Filho, J. S., Lopes, J. M., Martinho, O., Lambros, M. B., Martins, A., Schmitt, F., Pardal, F. and Reis, R. M. (2007) Molecular alterations of KIT oncogene in gliomas. Analytical Cellular Pathology. 29, pp. 399-408.

Han, L., Yang, Y., Yue, X., Huang, K., Liu, X., Pu, P., Jiang, H., Yan, W., Jiang, T. and Kang, C. (2010) Inactivation of PI3K/AKT signaling inhibits glioma cell growth through modulation of β-catenin-mediated transcription. Brain Res. 1366, pp. 9-17.

Horvath, S., Zhang, B., Carlson, M., Lu, K. V., Zhu, S., Felciano, R. M., Laurance, M. F., Zhao, W., Qi, S., Chen, Z., Lee, Y., Scheck, A. C., Liau, L. M., Wu, H., Geschwind, D. H., Febbo, P. G., Kornblum, H. I., Cloughesy, T. F., Nelson, S. F. and Mischel, P. S. (2006) Analysis of oncogenic signaling networks in glioblastoma identifies ASPM as a molecular target. Proc. Natl. Acad. Sci. U. S. A. 103, pp. 17402-17407. doi:10.1073/pnas.0608396103.

Kim, H., Park, T., & Gelenbe, E. (2014). Identifying disease candidate genes via large-scale gene network analysis. International journal of data mining and bioinformatics, 10(2), pp. 175-188.

Knight, K. and Fu, W. (2000) Asymptotics for lasso-type estimators. Annals of statistics. , pp. 1356-1378.

Kwiatkowska, A., Didier, S., Fortin, S., Chuang, Y., White, T., Berens, M. E., Rushing, E., Eschbacher, J., Tran, N. L. and Chan, A. (2012) The small GTPase RhoG mediates glioblastoma cell invasion. Mol Cancer. 11, pp. 65-72.

Li, C. and Li, H. (2008) Network-constrained regularization and variable selection for analysis of genomic data. Bioinformatics. 24, pp. 1175-1182. doi:10.1093/bioinformatics/btn081; 10.1093/bioinformatics/btn081.

Liang, Y., Liu, C., Luan, X. Z., Leung, K. S., Chan, T. M., Xu, Z. B. and Zhang, H. (2013) Sparse logistic regression with a L1/2 penalty for gene selection in cancer classification. BMC Bioinformatics. 14, 198-2105-14-198. doi:10.1186/1471-2105-14-198; 10.1186/1471-2105-14-198.

Liu, C., Liang, Y., Luan, X.Z., Leung, K.S., Chan, T.M., Xu, Z.B., Zhang, H. (2014) The L1/2 regularization method for variable selection in the Cox model. Applied Soft Computing, 14, pp. 498-503.

Liu, M., Liberzon, A., Kong, S. W., Lai, W. R., Park, P. J., Kohane, I. S. and Kasif, S. (2007) Network-based analysis of affected biological processes in type 2 diabetes models. PLoS Genet. 3, e96. doi:10.1371/journal.pgen.0030096.

Liu, Z., & Jiang, F. (2009). Gene identification and survival prediction with Lp Cox regression and novel similarity measure. International journal of data mining and bioinformatics, 3(4), pp. 398-408.

Lotsch, D., Engelmaier, C., Allerstorfer, S., Grusch, M., Pichler, J., Weis, S., Hainfellner, J., Marosi, C., Spiegl-Kreinecker, S. and Berger, W. (2013) fgfr4 inhibition impacts on glioblastoma aggressiveness in vitro and in vivo. 15, 13-13.

Malioutov, D., Çetin, M. and Willsky, A. S. (2005) A sparse signal reconstruction perspective for source localization with sensor arrays. Signal Processing, IEEE Transactions on. 53, pp. 3010-3022.

Mawrin, C., Diete, S., Treuheit, T., Kropf, S., Vorwerk, C. K., Boltze, C., Kirches, E., Firsching, R. and Dietzmann, K. (2003) Prognostic relevance of MAPK expression in glioblastoma multiforme. Int. J. Oncol. 23, pp. 641-648.

Meinshausen, N. and Yu, B. (2009) Lasso-type recovery of sparse representations for high-dimensional data. The Annals of Statistics., pp. 246-270.

Pelloski, C. E., Lin, E., Zhang, L., Yung, W. K., Colman, H., Liu, J. L., Woo, S. Y., Heimberger, A. B., Suki, D., Prados, M., Chang, S., Barker, F. G.,3rd, Fuller, G. N. and Aldape, K. D. (2006) Prognostic associations of activated mitogen-activated protein kinase and akt pathways in glioblastoma. Clin. Cancer Res. 12, 3935-3941. doi:10.1158/1078-0432. CCR-05-2202.

Rivals, I. and Personnaz, L. (2003) Mlps (mono layer polynomials and multi layer perceptrons) for nonlinear modeling. The Journal of Machine Learning Research. 3, pp. 1383-1398.

Robinson, J. P., Vanbrocklin, M. W., McKinney, A. J., Gach, H. M. and Holmen, S. L. (2011) Akt signaling is required for glioblastoma maintenance in vivo. Am. J. Cancer. Res. 1, pp. 155-167.

Sahai, E. and Marshall, C. J. (2002) RHO-GTPases and cancer. Nature Reviews Cancer. 2, pp. 133-142.

Shida, D., Takabe, K., Kapitonov, D., Milstien, S. and Spiegel, S. (2008) Targeting SphK1 as a new strategy against cancer. Curr. Drug Targets. 9, pp. 662-673.

Shen, Y., Liu, Z., & Ott, J. (2012). Support Vector Machines with L 1 penalty for detecting gene-gene interactions. International journal of data mining and bioinformatics, 6(5), pp. 463-470.

Sun, H., Lin, W., Feng, R., Li, H. (2014) Network-Regularized High-Dimensional Cox Regression for Analysis of Genomic Data. Statistica Sinica. 24, pp. 1433-1459.

Tibshirani, R. (1996) Regression shrinkage and selection via the lasso. Journal of the Royal Statistical Society.Series B (Methodological). , pp. 267-288.

Tu, Y., Zhong, Y., Fu, J., Cao, Y., Fu, G., Tian, X. and Wang, B. (2011) Activation of JAK/STAT signal pathway predicts poor prognosis of patients with gliomas. Medical Oncology. 28, pp. 15-23.

Turenne, N., & Schwer, S. R. (2008). Temporal representation for gene networks: towards a qualitative temporal data mining. International journal of data mining and bioinformatics, 2(1), pp. 36-53.

Van Brocklyn, J. R., Jackson, C. A., Pearl, D. K., Kotur, M. S., Snyder, P. J. and Prior, T. W. (2005) Sphingosine kinase-1 expression correlates with poor survival of patients with glioblastoma multiforme: Roles of sphingosine kinase isoforms in growth of glioblastoma cell lines. Journal of Neuropathology & Experimental Neurology. 64, pp. 695-705.

Wei, Z. and Li, H. (2007) A markov random field model for network-based analysis of genomic data. Bioinformatics. 23, 1537-1544. doi:10.1093/bioinformatics/btm129.

Xu, Z., Chang, X., Xu, F. and Zhang, H. (2012) Regularization: A thresholding representation theory and a fast solver. Neural Networks and Learning Systems, IEEE Transactions on. 23, pp. 1013-1027.

Xu, Z.B., Zhang, H., Wang, Y., Chang, X.Y., Liang, Y. (2010) L1/2 regularization. Sci China Series F. 40(3): pp. 1-11.

(56) References Cited

PUBLICATIONS

Zhang, W., Wan, Y., Allen, G. I., Pang, K., Anderson, M. L. and Liu, Z. (2013) Molecular pathway identification using biological network-regularized logistic models. BMC Genomics. 14, S7.

Zhu, Y., Pan, W. and Shen, X. (2009) Support vector machines with disease-gene-centric network penalty for high dimensional microarray data. Stat. Interface. 2, pp. 257-269.

Zou, H. (2006) The adaptive lasso and its oracle properties. Journal of the American statistical association. 101, pp. 1418-1429.

* cited by examiner

METHOD AND SYSTEM FOR DETERMINING AN ASSOCIATION OF BIOLOGICAL FEATURE WITH MEDICAL CONDITION

TECHNICAL FIELD

The present invention relates to a method and a system for determining an association of a biological feature with a medical condition, in particularly but not exclusively, to a method and a system for determining a biomarker and/or an indicator for a medical condition.

BACKGROUND

Currently, various statistical approaches are available for analyzing a high dimensional dataset. The commonly used approaches include filter, wrapper and embedded methods. Filter methods evaluate each gene via discriminative power without considering a combined effect of the gene group (Dudoit et al., Journal of the American Statistical association. 97, 2002, 77-87). Wrapper methods utilize a particular learning method as the feature evaluation measurement to select the gene subsets regarding the minimization of the classification errors and build the final classifier (Rivals, I. and Personnaz, L. 3, 2003, 1383-1398). Golub et al. (Golub, T. O., et al. Science. 286, 1999, 531-537) also proposed a gene selection approach utilizing support vector machines (SVM) based on recursive feature elimination.

However, these methods are developed purely from gene expression data without utilizing any biological gene network knowledge. The results generated from these methods have poor accuracy and preciousness. Accordingly, these methods are not suitable for biological analysis in particular for determining the relationship between a biological feature with a disease.

There remains a strong need for systems and associated methods for determining an association of biological features like gene expression with a medical condition which are effective and ensure sufficient accuracy in case of high-dimensional microarray data.

SUMMARY OF THE INVENTION

In accordance with a first aspect of the present invention, there is provided a method of determining an association of at least one biological feature with a medical condition, comprising the steps of:
obtaining a dataset comprising biological data related to a plurality of samples each having a plurality of biological features;
applying at least some of the biological data to a regression model to determine and/or optimize parameters in the regression model thereby solving the regression model; and
processing the biological data using the solved regression model with a biological model to determine one or more biological features that are associated with the medical condition.

In an embodiment, the regression model includes $L_{1/2}$-regularized regression model.

In an embodiment, the biological model includes biological network information associated with the medical condition and the one or more biological features.

In an embodiment, the biological network information is arranged to represent a biological process, a molecular interaction and/or a reaction network associated with the biological features.

In an embodiment, the step of processing the biological data using the solved regression model with a biological model comprises the step of combining the biological data with the biological network information to determine one or more biological features that are associated with the medical condition.

In an embodiment, the biological network information is graph Laplacian regularized.

In an embodiment, the step of regularizing the biological network information includes an iterative transformation for obtaining at least one estimation representing the correlation between the one or more biological features and the medical condition.

In an embodiment, the iterative transformation includes an univariate half thresholding operation of a coordinate descent optimization of the regularized biological network information for obtaining the model.

In an embodiment, a thresholding representation of $$\frac{\sqrt[3]{54}}{4}(\lambda)^{\frac{2}{3}}$$

is used in the univariate half thresholding operation, wherein $\lambda$ denotes a regularization parameter.

In an embodiment, the regression model includes $L_{1/2}$ penalized network-constrained regression model.

In an embodiment, the at least one biological feature includes at least one of presence of a gene, gene expression, presence of a gene product or amount of a gene product, and the medical condition is cancer.

In an embodiment, the one or more biological features associated with the medical condition includes one or more biomarker and/or indicator arranged to represent an indication of the medical condition.

In accordance with a second aspect of the present invention, there is provided a system for determining an association of at least one biological feature with a medical condition, comprising a processing module arranged to:
apply at least some of the biological data in a dataset comprising biological data related to a plurality of samples each having a plurality of biological features to a regression model so as to determine and/or optimize parameters in the regression model thereby solving the regression model; and
process the biological data using the solved regression model with a biological model to determine one or more biological features that are associated with the medical condition.

In an embodiment, the regression model includes $L_{1/2}$ penalized network-constrained regression model.

In an embodiment, the biological model includes biological network information associated with the medical condition and the one or more biological features.

In an embodiment, the one or more processor is further arranged to combine the biological data with the biological network information so as to determine one or more biological features that are associated with the medical condition.

In an embodiment, the biological network information is graph Laplacian regularized.

In an embodiment, the one or more processor is arranged to perform an iterative transformation for obtaining at least one estimation representing the correlation between the one or more biological features and the medical condition.

In an embodiment, the iterative transformation includes an univariate half thresholding operation of a coordinate descent optimization of the regularized biological network information for obtaining the model.

In an embodiment, the at least one biological feature includes at least one of presence of a gene, gene expression, presence of a gene product or amount of a gene product, and the medical condition is cancer, and wherein the one or more biological features associated with the medical condition includes one or more biomarker and/or indicator arranged to represent an indication of the medical condition.

Other features and aspects of the invention will become apparent by consideration of the following detailed description and accompanying drawings.

was applied.

Figure 4:
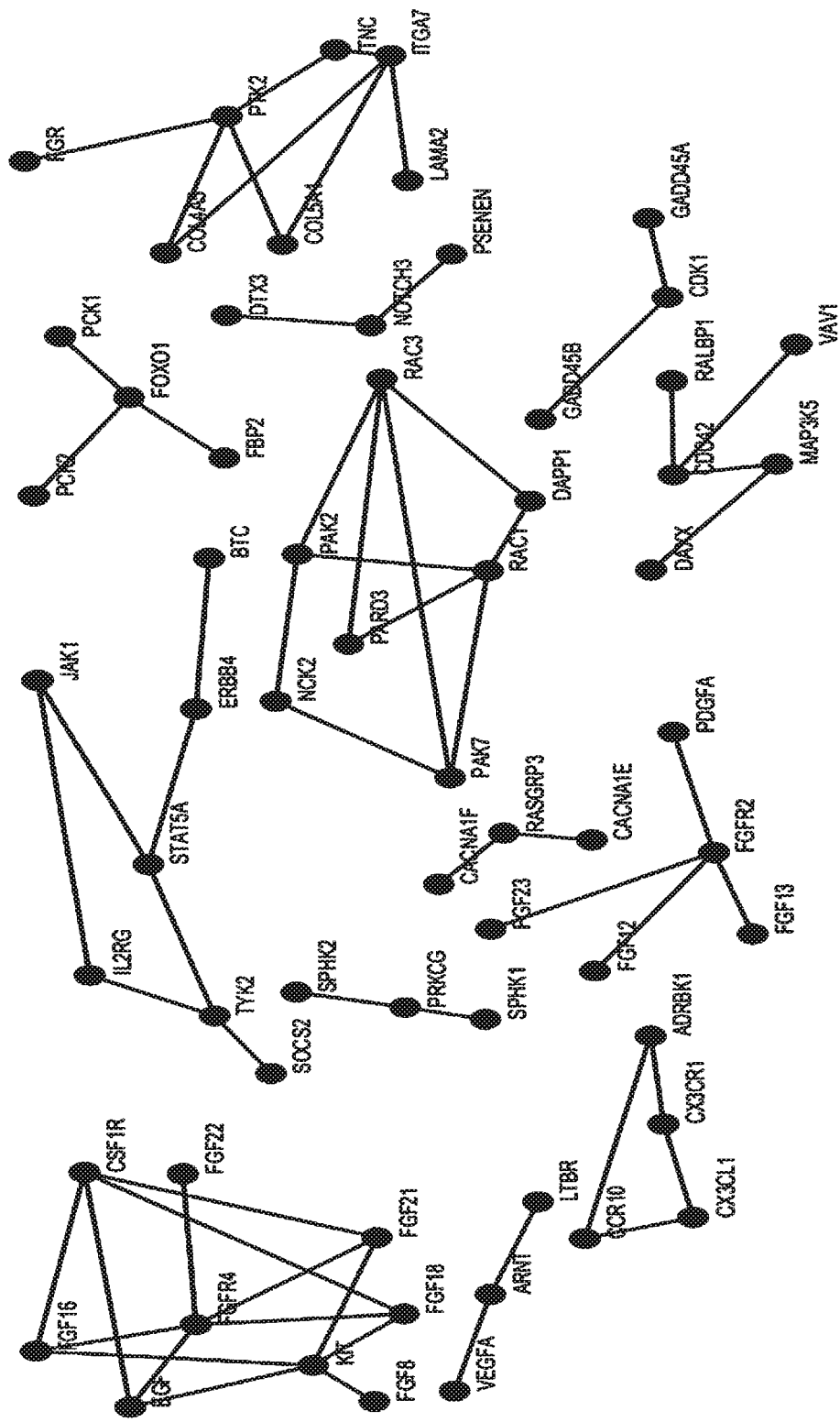

FIG. 4 shows the associations of various genes with glioblastoma determined from a system using solver $L_{1/2}$ penalty procedures, in which a thresholding representation of $$\frac{3}{4}(\lambda)^{\frac{2}{3}}$$

was applied.

Figure 5:
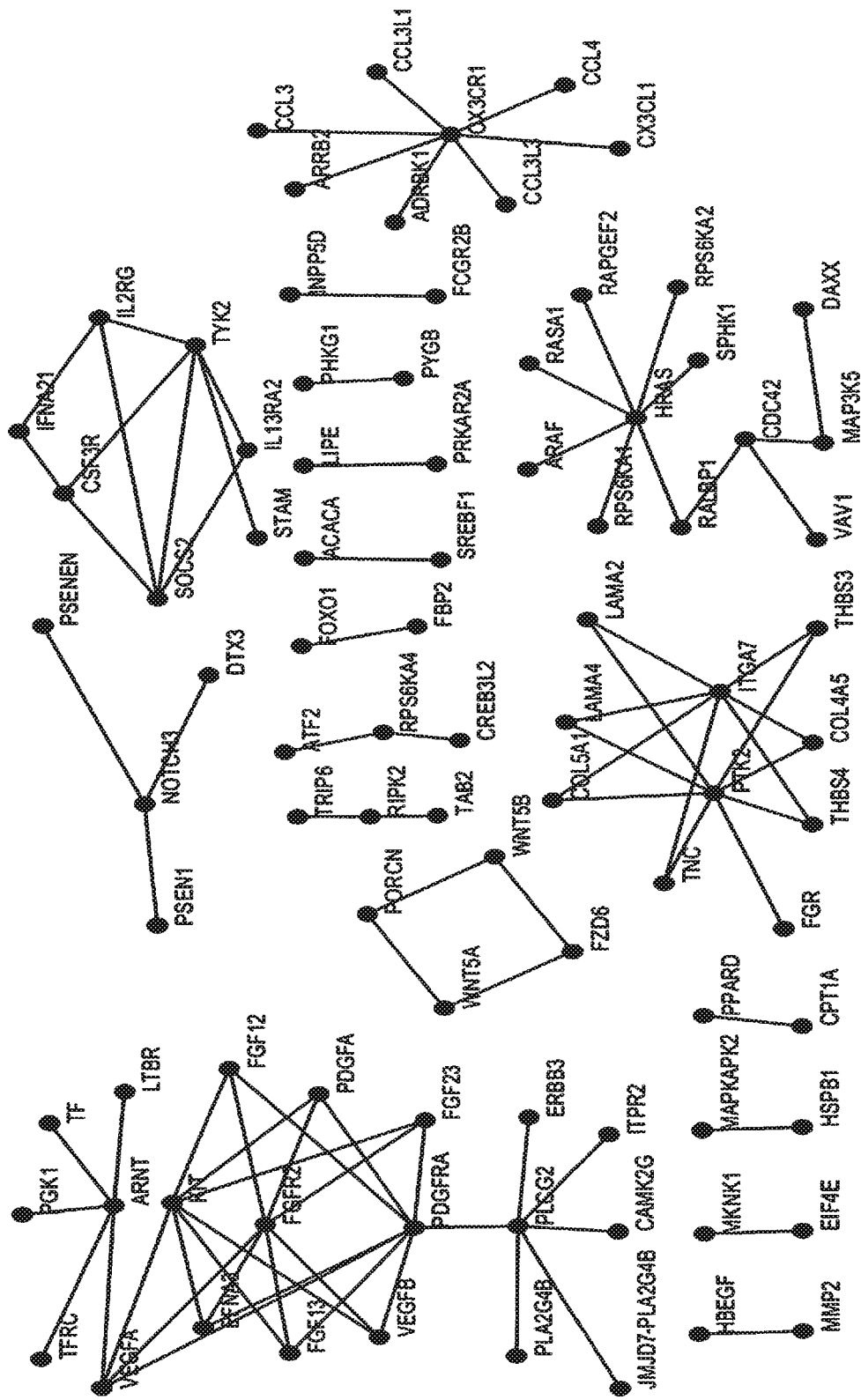

FIG. 5 shows the associations of various genes with glioblastoma determined from a system using solver $L_1$ penalty procedures, in which a thresholding representation of $$\frac{3}{4}(\lambda)^{\frac{2}{3}}$$

was applied.

DETAILED DESCRIPTION OF THE INVENTION

The inventors based on their research, tests and experiments found that various studies have revealed the relationships between genes and pathways for disease-related biological processes. In general, these relationships may be presented by biological network information such as a gene regulation network. The gene regulation network refers to a collection of effective interactions, and describes the multiple biological relations wherein one gene affects the others if they are connected. In the last decade, many databases have been established on distinct aspects of biological systems. For example, the KEGG pathway database (www.genome.jp/kegg/) records molecular interactions and relational networks at the levels of both cell and organism. Without being bound by theory, the inventors concluded that combining these valuable information of genes and pathways with a statistical model may shed light on how human cells work from a system-level perspective. Such a combination is also capable of identifying possible biomarkers and/or indicators for a medical condition such as a disease, in particular the combination is capable of identifying a gene that is highly associated with a disease though the gene may also exert a relatively weak effect under normal biological condition.

Several statistical methods have been developed to utilize the pathways or biological network information. For example, Wei and Li (Wei, Z. and Li, H. Bioinformatics. 23, 2007, 1537-1544) proposed a Markov random field-based approach, which joints the prior pathway to microarray data together to find affected pathway and relevant gene targets. Li and Li (Li, C. and Li, H. Bioinformatics. 24, 2008, 1175-1182) adopted the standard Laplacian strategy to construct a network-constrained regularization procedure for fitting linear regression models. Zhu et al. (Zhu, Y. et al. Stat. Interface. 2, 2009, 257-269) incorporated the prior pathway information into microarray-based classifiers for binary classification under support vector machine framework. Zhang et al. (Zhang et al. BMC Genomics. 14, 2013, S7) used normalized Laplacian approach to build the network-constrained logistic model for disease classification and prediction. Sun et al. (Sun et al. Statistica Sinica. 24, 2014, 1433-1459) combined network-constrained approach with Cox model for survival analysis.

However, high dimensionality of information is a problem encountered in the above approaches. Regularization methods have been used in microarray data analysis to deal with such a problem. A well-known regularization method is the $L_1$ (LASSO) type regularization methods. However, the $L_1$ regularization may yield inconsistent results when applied to variable selection in some situations and often introduce extra bias in estimation. To solve the high dimensional problems, a more sparse solution is necessary for interpretation but the $L_1$ regularization fails to meet this requirement.

Thus, there remains a need for an improved statistical model to be applied in a system or a method for determining an association of at least one biological feature with a medical condition. It is believed that the $L_q$ (0<q<1) regularizations can assuredly generate more sparse solutions than $L_1$ regularization. Moreover, the $L_{1/2}$ penalty can be taken as a representative of $L_q$ (0<q<1) penalty because it has many promising advantages including unbiasedness, sparsity and oracle properties.

Without being bound by theory, the inventors herein through their research, tests and experiments discovered that a novel network-constrained regression model with $L_{1/2}$ penalization can be applied in a system to select one or more suitable biomarkers from biological data and the selected biomarkers are closely associated with a targeted medical condition, pathway etc. It is believed that the model of the system of the present invention shows promising prediction accuracy and biomarker selection.

In this embodiment, the system for determining an association of at least one biological feature with a medical condition is implemented by or for operation on a computer having an appropriate user interface. The computer may be implemented by any computing architecture, including stand-alone PC, client/server architecture, "dumb" terminal/mainframe architecture, or any other appropriate architecture. The computing device is appropriately programmed to implement the invention.

Figure 1:
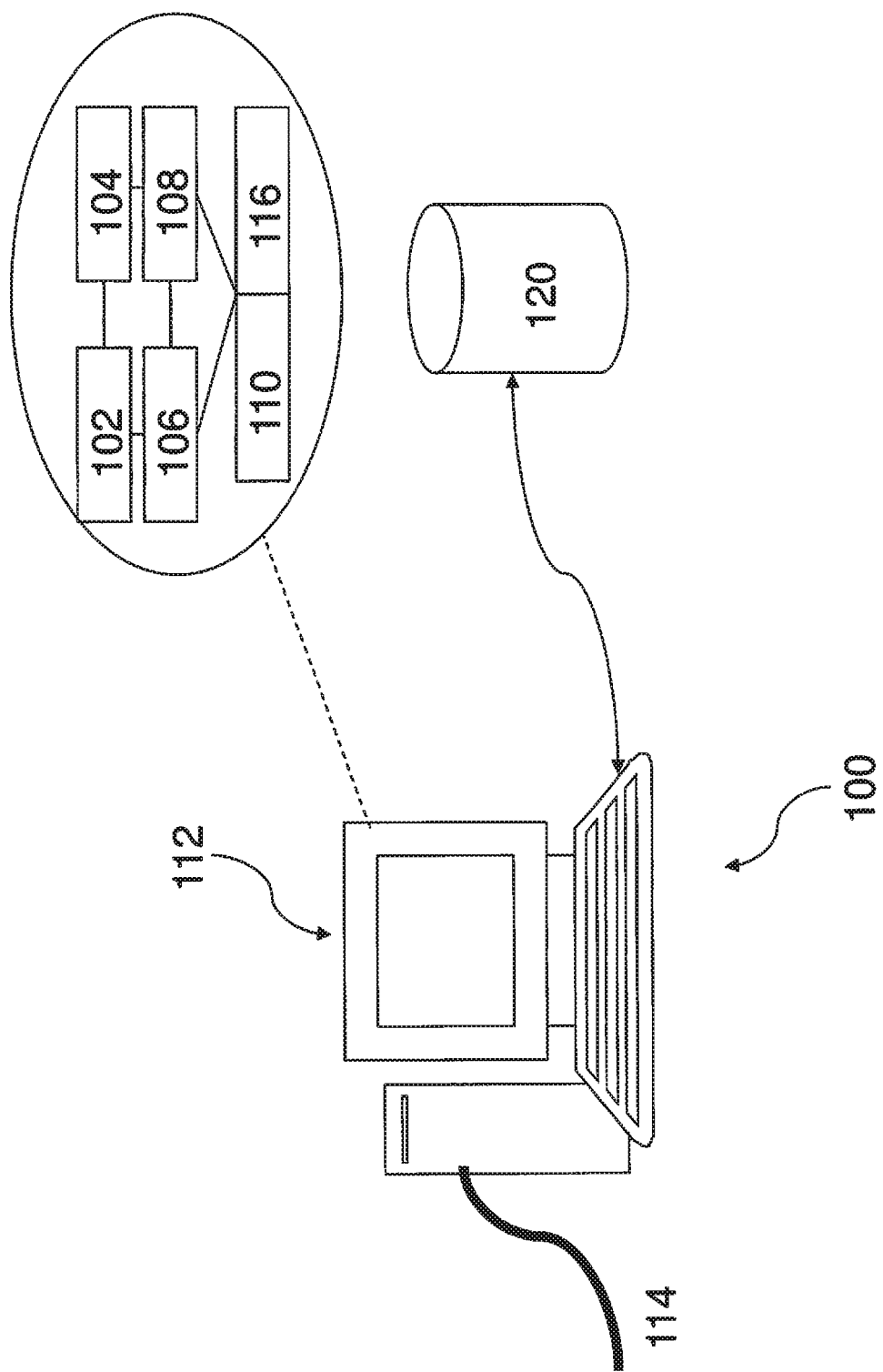
FIG. 1 is a schematic diagram of a computer or computing server arranged to operate a system of the present invention for determining an association of at least one biological feature with a medical condition.

Referring to FIG. 1, there is shown a schematic diagram of a computer or a computing server 100 which in this embodiment comprises a server 100 arranged to operate, at least in part if not entirely, the system for determining an association of at least one biological feature with a medical condition in accordance with one embodiment of the present invention. The server 100 comprises suitable components necessary to receive, store and execute appropriate computer instructions. The components may include a processing unit 102, read-only memory (ROM) 104, random access memory (RAM) 106, and input/output devices such as disk drives 108, input devices 110 such as an Ethernet port, a USB port, etc., a display 112 such as a liquid crystal display, a light emitting display or any other suitable display and communications links 114. The server 100 includes instructions that may be included in ROM 104, RAM 106 or disk drives 108 and may be executed by the processing unit 102. There may be provided a plurality of communication links 114 which may variously connect to one or more computing devices such as a server, personal computers, terminals, wireless or handheld computing devices. At least one of a plurality of communications link may be connected to an external computing network through a telephone line or other type of communications link.

The server 100 may include storage devices such as a disk drive 108 which may encompass solid state drives, hard disk drives, optical drives or magnetic tape drives. The server 100 may use a single disk drive or multiple disk drives. The server 100 may also have a suitable operating system. 116 which resides on the disk drive or in the ROM of the server 100.

The system has a database 120 residing on a disk or other storage device which is arranged to store a dataset. The database 120 is in communication with the server 100 with an interface, which is implemented by computer software residing on the server 100. Alternatively, the database 120 may also be implemented as a stand-alone database system in communication with the server 100 via an external computing network, or other types of communication links.

Figure 2:
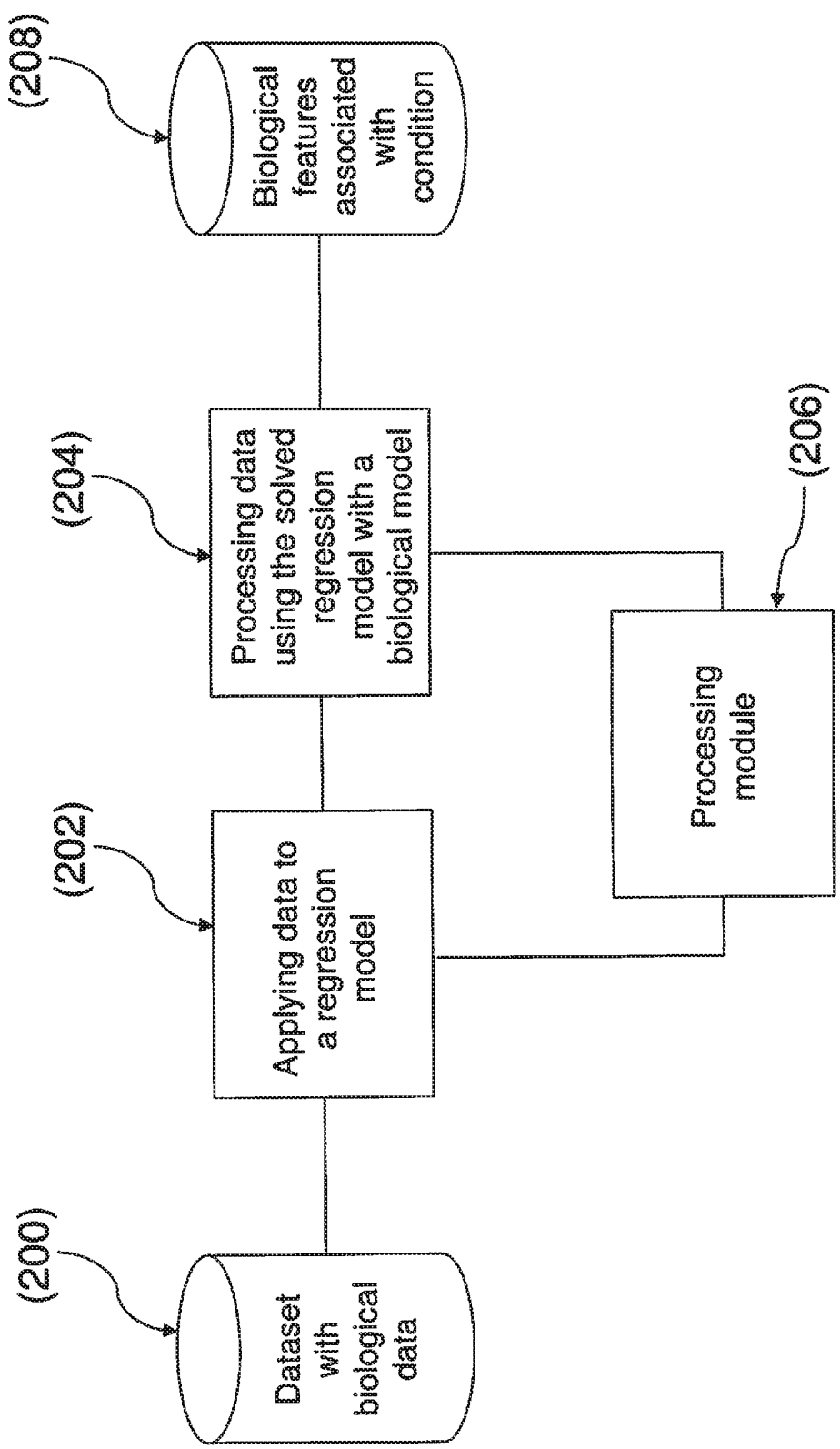
FIG. 2 is a schematic diagram showing a system of the present invention for determining an association of at least one biological feature with a medical condition.

With reference to FIG. 2, there is provided an embodiment of a system for determining an association of at least one biological feature with a medical condition, comprising a processing module (206) arranged to:
  apply at least some of the biological data in a dataset comprising biological data (200) related to a plurality of samples each having a plurality of biological features to a regression model (202) so as to determine and/or optimize parameters in the regression model thereby solving the regression model; and
  process the biological data using the solved regression model with a biological model (204) to determine one or more biological features that are associated with the medical condition (208).

In this embodiment, the system may include a processing module arranged to apply at least some of the biological data in a dataset comprising biological data related to a plurality of samples from humans each having a plurality of biological features including gene expression to a regression model so as to determine and/or optimize parameters in the regression model thereby solving the regression model, wherein the regression model includes $L_{1/2}$ regularized regression model.

The processing module is further arranged in this embodiment to process the biological data using the solved regression model with a biological model including biological network information associated with a medical condition such as cancer to determine one or more biological features, e.g. one or more gene expression, that are associated with the medical condition. The biological network information in general represents a biological process, a molecular interaction and/or a reaction network associated with one or more biological features.

The one or more biological features are obtained from a biological sample such as a human patient. In particular, the biological feature includes at least one of presence of a gene, gene expression, presence of a gene product or amount of a gene product These processes, which can include methods of the present invention, may be implemented as a plurality of steps on a computer or computing device, such as those as found in FIG. 1.

The system of the present invention utilizing in an embodiment a novel $L_{1/2}$ regularized regression model is especially suitable and highly advantageous for selecting significantly relevant biomarkers and/or indicator in high dimensional biological datasets and can include construction of a gene-gene network that are closely related to each in a relevant biological pathway for a medical condition. The $L_{1/2}$ regularized regression model may be $L_{1/2}$ penalized network-constrained regression model.

Experimental results confirmed that novel $L_{1/2}$ penalized network-constrained regression model utilized by the system of the present invention in an embodiment has a good performance in particular in the high-dimensional and microarray data environment. Simulation studies and real data experiments confirmed that the performance of this model outperforms other regularized methods. Thus, the regression model of the present invention is highly advantageous as it allows selecting less but more effective targets for a biomarker and/or indicator identification.

The system of the present invention may, thus, have a significant impact on diagnosis and treatment decisions for treating a medical condition such as cancer. In particular, it can be used for constructing a simple and satisfactory gene-gene network with gene-expression profile for cancer diagnosis in a fast and accurate way.

Preferably but not exclusively, the system of the present invention can be used for classification, disease-related gene selection. The genes selected by the system can be seen as the molecular interaction information about the disease-related biological process, and then they can be gathered from some biological databases, such as KEGG pathway database. The constructed model which combines the biological network information associated with a medical condition and molecular interaction information extracted from the biological process with analysis of the gene expression data has been proved for being biologically meaningful and can remove the noise effectively.

In the system and method of the present invention, the medical condition refers to any physiologic, mental or psychological condition or disorder. For example, the medical condition may be a cancer, an inflammation and so forth.

Further features, applications and advantages of the system and method of the present invention will be evident for a person skilled in the art from the features and embodiments described below relating to a $L_{1/2}$ solver penalized network-constraint regression model.

In one embodiment, a biological network is integrated into an analysis of the gene expression data by applying a graph Laplacian constraint approach (Li, C. and Li, H., Bioinformatics. 24, 2008, 1175-1182). Consider a graph G=(V, E), where V is the set of genes that meet to the p explanatory variables, E is the adjacency matrix. If u and v is linked, then $e_{uv}=1$, otherwise $e_{uv}=0$. The normalized Laplacian matrix L for G is defined by:

$$L_{uv} = \begin{cases} 1 - w_{uv}/d_u & \text{if } u = v \text{ and } d_u \neq 0, \\ -w_{uv}/\sqrt{d_u d_v} & \text{if } u \text{ and } v \text{ are adjacent}. \\ 0 & \text{otherwise} \end{cases}$$

where $d_u$ and $d_v$ are the degrees of gene u and v respectively. For any fixed non-negative λ, the network constrained linear regression model is:

$$L(\lambda, \beta) = (y - X\beta)^T (y - X\beta) + \lambda \beta^T L \beta \quad (1),$$

where the first term in Equation (1) is the linear regression model. The second term is a generalized $L_2$-norm penalty function based on the graphical Laplacian matrix, which facilitates the smooth solution of β in the biological network.

For a high dimensional application with the number of genes p>>the sample size n, solving Equation (1) directly is ill-posed and may lead to overfitting. The system of the present invention is advantageous in that it solves such an overfitting problem by adding a regularization term to Equation (1). Accordingly, the sparse network constrained regression can be modeled as:

$$L(\lambda_1, \lambda_2, \beta) = (y - X\beta)^T (y - X\beta) + \lambda_1 P(\beta) + \lambda_2 \beta^T L \beta \quad (2)$$

where $\lambda_1, \lambda_2 > 0$ are regularization parameters.

In general, Lasso type ($L_1$) regularization having the regularization term $$P(\beta) = \sum_{j=1}^{p} |\beta_j|$$

can be applied. However, Lasso type ($L_1$) regularization does not provide satisfactory results in biological researches such as determination of biomarkers and determination of the association between genes and a medical condition. For example, the results have poor sparsity. Studies have shown that $L_1$ regularization approaches are asymptotically biased. Theoretically, within $L_q$ (0<q<1) type regularization $|\beta|_q = \Sigma |\beta|^q$, the smaller value of q refers to the more sparse to the solutions and gives asymptotically unbiased estimates. However, the $L_q$ regularization is a non-convex, non-smooth, and non-Lipschitz optimization problem. Some studies also explored the properties of $L_q$ (0<q<1) regularization and concluded that $L_q$ regularizations with q∈(0, 1), only $L_{1/2}$ and $L_{2/3}$ regularizations permit an analytically expressive thresholding representation. In other words, the sparsity of $L_{2/3}$ regularization performs not as well as $L_{1/2}$ regularization.

The inventors discovered that $L_{1/2}$ regularization can be used in the system of the present invention for determining an association of at least one biological feature with a medical condition along with a biological model such as biological network information. The combination of the $L_{1/2}$ regularization and a biological model allows an unbiased, higher sparsity and oracle approach for biological information analysis such as determination of an appropriate biomarker for a disease diagnosis, a status check of a condition, a targeted drug therapy, and a determination of suitable target for targeted drug therapy.

The present invention applies a novel $L_{1/2}$ thresholding representation so as to attain a more efficient system and method for determining an appropriate biomarker from a dataset such as a high-dimensional size microarray data.

In an embodiment, the system is capable of combining biological information such as biological pathways information with gene-expression data for determining one or more biological features that are associated with a medical condition. In this embodiment, the biological feature may serve as a biomarker for study of the medical condition.

The $L_{1/2}$ penalized network constrained regression model used in the system of the present invention is represented by the following equation:

$$[L(\lambda_1, \lambda_2, \beta) = (y - X\beta)^T (y - X\beta) + \lambda_1 |\beta|_{1/2} + \lambda_2 \beta^T L \beta] \quad (3)$$

where $$|\beta|_{1/2} = \sum_{j=1}^{p} |\beta_j|^{1/2}, \quad \beta^T L \beta = \sum_{e_{uv} \neq 0} \left(\frac{\beta_u}{d_u} - \frac{\beta_v}{d_u}\right)^2$$

The inventors developed a coordinate descent method for the $L_{1/2}$ penalized network-constraint using a novel thresholding representation. The $L_{1/2}$ penalty function is non-convex, which raises numerical challenges in fitting the models. Recently, coordinate descent methods for solving non-convex regularization models (SCAD, MCP) have demonstrated significant efficiency to converge. The methods optimize a target function with respect to a single parameter at a time, and iteratively cycle through all parameters until their convergence reached (Breheny, P. and Huang, J. Ann. Appl. Stat. 5, 2011, 232-253). Since the computational burden increases only linearly with the feature number p, coordinate descent methods are considered as a possible tool for solving high-dimensional problems. The respective standard procedures are as follows: for every coefficient, to partially optimize the target function with respect to $\beta_j$ (j=1, 2, . . . , p) with the remaining elements of β fixed at their most recently updated values.

Suppose that the dataset has n observations with p genes. Let $y = (y_1, \ldots, y_n)^T$ be the corresponding response and $X = [x_1|, \ldots, |x_p]$ be the matrix of biomarkers measured on n samples with $x_j = (x_{1j}, \ldots, x_{nj})^T$ for j=1, . . . , p genes. Assume the variables are standardized:

$$\sum_{i=1}^{n} x_{ij} = 0, \quad n^{-1} \sum_{i=1}^{n} x_{ij}^2 = 1 \text{ and } \sum_{i=1}^{n} y_i = 0.$$

Thus, the linear regression with the regularization term can be expressed as:

$$L(\beta) = \text{argmin}\left\{\frac{1}{n} \sum_{i=1}^{n} (y_i - X'\beta)^2 + \lambda \sum_{j=1}^{p} P(\beta_j)\right\} \quad (4)$$

where the P(β) is the regularization term. The coordinate descent method solves $\beta_i$ and other $\beta_{k \neq j}$ (k≠j represent the parameters remained after $j^{th}$ element is removed) are fixed. Equation (4) can be rewritten as:

$$L(\beta) = \operatorname{argmin}\left\{\frac{1}{n}\left(y_i - \sum_{k \neq j} x_{ik}\beta_k - x_{ij}\beta_j\right)^2 + \lambda \sum_{k \neq j} P(\beta_k) + \lambda P(\beta_j)\right\} \quad (5)$$

The first order derivative at $\beta_j$ can be estimated as:

$$\left[\frac{\partial L}{\partial \beta_j} = \frac{1}{n}\sum_{i=1}^{n}\left(-x_{ij}\left(y_i - \sum_{k \neq j} x_{ik}\beta_k - x_{ij}\beta_j\right)\right) + \lambda P(\beta_j)' = 0\right] \quad (6)$$

Define $\tilde{y}_i^{(j)} = \sum_{k \neq j} x_{ik}\beta_k$ as the partial residual for fitting $\beta_j$, and $$\omega_j = \sum_{i=1}^{n} x_{ij}(y_i - \tilde{y}_i^{(j)}),$$

the univariate soft thresholding operator of the coordinate descent method for the $L_1$ regularization (Lasso) can be defined as:

$$\beta_j = S(\omega_j, \lambda) = \begin{cases} \omega_j + \lambda & \text{if } \omega_j < -\lambda \\ \omega_j - \lambda & \text{if } \omega_j > \lambda \\ 0 & \text{if } |\omega_j| < \lambda \end{cases} \quad (7)$$

Similarly, for the $L_0$ regularization, the thresholding operator of the coordinate descent method can be defined as:

$$\beta_j = \operatorname{Hard}(\omega_j, \lambda) = \omega I(|\omega_j| > \lambda) \quad (8)$$

where I is the indicator function. This formula is equivalent to the hard thresholding operator. According to Equations (7) and (8), it was found that different penalties are associated with different thresholding operators. Therefore, it is proposed that a half thresholding operator can be applied to solve the $L_{1/2}$ regularization for linear regression model. In this embodiment, a novel univariate half thresholding operator of the coordinate descent method for the $L_{1/2}$ regularization is applied. It is recognized as an iterative method, i.e. an iterative transformation, and can be considered as a multivariate half thresholding approach.

Based on Equation (6), the gradient of the $L_{1/2}$ regularization at $\beta_j$ can be expressed as:

$$\beta_j = \operatorname{New\_Half}(\omega_j, \lambda) = \quad (9)$$

$$\begin{cases} \frac{2}{3}\omega_j\left(1 + \cos\left(\frac{2(\pi - \varphi_\lambda(\omega_j))}{3}\right)\right) & \text{if } |\omega_j| > \frac{\sqrt[3]{54}}{4}(\lambda)^{\frac{2}{3}} \\ 0 & \text{otherwise} \end{cases}$$

where $\varphi_\lambda(\omega) = \arccos\left(\frac{\lambda}{8}\left(\frac{|\omega|}{3}\right)^{-\frac{3}{2}}\right)$.

The inventors previously applied $$\frac{3}{4}(\lambda)^{\frac{2}{3}}$$

to represent $L_{1/2}$ regularization thresholding operator. The inventors further discovered that the novel half thresholding representation $$\frac{\sqrt[3]{54}}{4}(\lambda)^{\frac{2}{3}}$$

can be applied in the system. This novel thresholding operator is found to be more precise and effective than the previous one. The quantity of the regularization solutions depends significantly on the setting of the regularization parameter $\lambda$. Based on this novel thresholding operator, when $\lambda$ is chosen by some efficient parameters tuning strategies, such as cross-validation, the convergence of the method is proved.

The Equation (2) of $L_{1/2}$ regularization combined with the network-network constraint can be modeled as:

$$L(\lambda_1, \lambda_2, \beta) = L(\gamma, \beta^*) = (y^* - X^*\beta^*)^T(y^* - X^*\beta^*) + \sum_{j=1}^{p} |\beta_j^*|^{1/2} \quad (10)$$

where $L = U\Gamma U^T$ and $S = U\Gamma^{1/2}$, Let $\gamma = \lambda_1/\sqrt{1+\lambda_2}$ and $\beta^* = \sqrt{1+\lambda_2}\beta$, $$L(\lambda_1, \lambda_2, \beta) = (\gamma, \beta^*) = (y^* - X^*\beta^*)^T(y^* - X^*\beta^*) + \sum_{j=1}^{p} |\beta_j^*|^{1/2} \quad (10)$$

where $L = U\Gamma U^T$ and $S = U\Gamma^{1/2}$,

Let $\gamma = \lambda_1/\sqrt{1+\lambda_2}$ and $\beta^* = \sqrt{1+\lambda_2}\beta$, $$X^*_{(n+p)\times p} = (1+\lambda_2)^{-1/2}\binom{X}{\sqrt{\lambda_2} sT}, Y^*_{(n+p)} = \binom{Y}{0}.$$

Accordingly, the coordinate descent method is directly applied to the $L_{1/2}$ penalized network-constraint regression model, and the details are given as follows:

Step 1: Initialize all $\beta_j(m)=0$ (j=1, 2, . . . , p) and $y^+$, $X^+$, set m=0, $\gamma$ is chosen by cross-validation;

Step 2: Approximate the loss function (10) based on the current $\beta(m)$;

Step 3: Update each $\beta_j(m)$, and cycle over j=1, . . . , p, until $\beta_j(m)$ does not change;

Step 3.1: Calculate $$\hat{y}_i^{(j)}(m) = \sum_{k \neq j} x_{ik}\beta_k \text{ and } \omega_j(m) = \sum_{i}^{n} x_{ij}(y_i(m) - \hat{y}_i^{(j)}(m));$$

Step 3.2: Update $\beta_j(m) = \operatorname{New\_Half}(\omega_j(m), \gamma)$;

Step 4: Let m=m+1) $\beta(m+1) \leftarrow \beta(m)$;

repeat Steps 2, 3 until $\beta(m)$ convergence.

Experiments have proved that this method of using the $L_{1/2}$ penalized network-constrained linear regression works well in the feature extraction problems. It is because the procedure does not need to tune many irrelevant parameters and does not need to recalculate partial residuals for each update step.

The parameter estimation, model selection and prediction capability of the three penalized network-constrained regression models were further evaluated:

$L_1$, $L_{1/2}$ with a thresholding $$\frac{3}{4}(\lambda)^{\frac{2}{3}}$$

previously studied; and $L_{1/2}$ with the novel solver $$\frac{\sqrt[3]{54}}{4}(\lambda)^{\frac{2}{3}}.$$

A Model 1 was firstly established. A graph structure was simulated to mimic gene regulatory network: assuming that the graph consisted of 200 unconnected transcription factors (TFs), and each TF may regulate 10 different genes, so there are a total 2200 variables, $X=(x_1, x_2, \ldots, x_p)$, p=2200. Each $x_i$ (i=1, ..., p) is generated by the normal distribution N(0,1) firstly, then if $x_m$ regarding the gene regulated by TF $x_n$, $x_m = r \times x_m + (1-r) \times x_n$, where r is the correlation coefficient of the gene $x_m$ and its regulated TF $x_n$. It is also assumed that the response y, which is associated with the matrix X of TFs and their regulated genes, is calculated based on the following formula:

$$y = X\beta + \epsilon$$

where $$\beta = \left(4, \underbrace{\frac{4}{\sqrt{10}}, \ldots, \frac{4}{\sqrt{10}}}_{10}, -4, \underbrace{\frac{-4}{\sqrt{10}}, \ldots, \frac{-4}{\sqrt{10}}}_{10}, 8, \right.$$
$$\left. \underbrace{\frac{8}{\sqrt{10}}, \ldots, \frac{8}{\sqrt{10}}}_{10}, -8, \underbrace{\frac{-8}{\sqrt{10}}, \ldots, \frac{-8}{\sqrt{10}}}_{10}, 0, \ldots, 0\right)$$

for Model 1, and $\epsilon \sim N(0, \sigma_\epsilon^2)$, and $\epsilon \sim N(0, \sigma_\epsilon^2)$, and $\epsilon \sim N(0, \sigma_e^2)$. Thus, the regulatory network contains 44 edges connected between first 4 TFs and their relevant genes.

For Model 2, the variables were generated in the same way as Model 1, but considered the case where the regulated genes have positive and negative effects at the same time.

$$\beta = \left(4, \frac{-4}{\sqrt{10}}, \frac{-4}{\sqrt{10}}, \frac{-4}{\sqrt{10}}, \underbrace{\frac{4}{\sqrt{10}}, \ldots, \frac{4}{\sqrt{10}}}_{7}, -4, \frac{4}{\sqrt{10}}, \frac{4}{\sqrt{10}}, \frac{4}{\sqrt{10}},\right.$$

$$\underbrace{\frac{-4}{\sqrt{10}}, \ldots, \frac{-4}{\sqrt{10}}}_{7}, 8, \frac{-8}{\sqrt{10}}, \frac{-8}{\sqrt{10}}, \frac{-8}{\sqrt{10}}, \underbrace{\frac{8}{\sqrt{10}}, \ldots, \frac{8}{\sqrt{10}}}_{7},$$

$$\left.8, \frac{8}{\sqrt{10}}, \frac{8}{\sqrt{10}}, \frac{8}{\sqrt{10}}, \underbrace{\frac{-8}{\sqrt{10}}, \ldots, \frac{-8}{\sqrt{10}}}_{7}, 0, \ldots, 0\right)$$

In Model 2, first three ones of the 10 genes regulated by the TF had different signs from the other 7 genes.

The third model is similar to Model 1, except that $\sqrt{10}$ in the denominators in β was replaced with 8. The fourth model is similar to Model 2, which assumes that genes that are regulated by the same TF can have both positive and negative effects on the response Y. For this model, $\sqrt{10}$ in the denominators in β was replaced with 8.

For each model, the respective simulated data consisted of a training set and an independent test set with 120 sample size. 10-fold cross validation approach was conducted on the training dataset to tune the regularization parameters. For these models, the simulations were repeated over 60 times, and the performance with the prediction mean-squared error (PMSE), sensitivity and specificity for each model were evaluated. The sensitivity and specificity were defined as following:

$$\text{True Negative }(TN) := \left|\bar{\beta}.*\overline{\hat{\beta}}\right|_0, \text{False Positive }(FP) := \left|\bar{\beta}.*\hat{\beta}\right|_0$$

$$\text{False Negative }(FN) := \left|\beta.*\overline{\hat{\beta}}\right|_0, \text{True Positive }(TP) := \left|\beta.*\hat{\beta}\right|_0$$

$$\text{Sensitivity} := \frac{TP}{TP+FN}, \text{Specificity} := \frac{TN}{TN+FP}.$$

where the ·* is the element-wise product, and $|\cdot|_0$ calculates the number of non-zero elements in a vector, $\bar{\beta}$ and $\overline{\hat{\beta}}$ are the logical "not" operators on the vectors β and $\hat{\beta}$.

Table 1 summarizes the simulation results from each model with different correlation coefficients 0.3 and 0.9. For four models, most of times, the network-constrained regression with the novel $L_{1/2}$ penalty method of the present invention gave smaller PMSEs when compared with the network-constrained regression with $L_1$ penalty and the $L_{1/2}$ penalty with the solver previously investigated. Meanwhile, the approach with the novel $L_{1/2}$ penalty has much higher sensitivity for selecting the relevant genes and also attains a better performance in specificity. Table 1 shows that the novel $L_{1/2}$ penalty method is better than the $L_1$ method and the $L_{1/2}$ using a thresholding $$\frac{3}{4}(\lambda)^{\frac{2}{3}}$$

in term of prediction accuracy and variable selection in the different variable correlation and noise situations.

TABLE 1

| | | PMSE | | | Sensitivity | | | Specificity | | |
|---|---|---|---|---|---|---|---|---|---|---|
| | Model | Novel $L_{1/2}$ | $L_{1/2}$ | $L_1$ | Novel $L_{1/2}$ | $L_{1/2}$ | $L_1$ | Novel $L_{1/2}$ | $L_{1/2}$ | $L_1$ |
| r = 0.3 | 1 | 19.22 (5.36) | 20.87 (5.62) | 27.85 (6.22) | 0.872 (0.02) | 0.866 (0.02) | 0.818 (0.02) | 0.955 (0.01) | 0.966 (0.01) | 0.922 (0.01) |

TABLE 1-continued

Results obtained from four models.

|  | Model | PMSE Novel $L_{1/2}$ | $L_{1/2}$ | $L_1$ | Sensitivity Novel $L_{1/2}$ | $L_{1/2}$ | $L_1$ | Specificity Novel $L_{1/2}$ | $L_{1/2}$ | $L_1$ |
|---|---|---|---|---|---|---|---|---|---|---|
|  | 2 | 31.76 | 33.93 | 34.11 | 0.852 | 0.849 | 0.863 | 0.988 | 0.981 | 0.927 |
|  |  | (7.63) | (7.66) | (8.63) | (0.01) | (0.01) | (0.01) | (0.01) | (0.01) | (0.01) |
|  | 3 | 17.05 | 17.12 | 25.69 | 0.894 | 0.881 | 0.833 | 0.953 | 0.953 | 0.929 |
|  |  | (5.01) | (5.62) | (5.12) | (0.01) | (0.01) | (0.01) | (0.01) | (0.01) | (0.01) |
|  | 4 | 20.76 | 20.83 | 23.48 | 0.869 | 0.86 | 0.863 | 0.967 | 0.964 | 0.932 |
|  |  | (4.63) | (4.66) | (4.3) | (0.01) | (0.01) | (0.01) | (0.00) | (0.01) | (0.00) |
| r = 0.9 | 1 | 19.19 | 19.72 | 24.11 | 0.882 | 0.872 | 0.833 | 0.998 | 0.981 | 0.957 |
|  |  | (4.99) | (4.66) | (5.63) | (0.01) | (0.01) | (0.00) | (0.01) | (0.02) | (0.01) |
|  | 2 | 23.19 | 25.72 | 28.11 | 0.821 | 0.812 | 0.803 | 0.967 | 0.961 | 0.967 |
|  |  | (6.21) | (6.66) | (7.41) | (0.01) | (0.02) | (0.02) | (0.02) | (0.02) | (0.01) |
|  | 3 | 16.55 | 16.81 | 21.37 | 0.891 | 0.889 | 0.857 | 0.987 | 0.980 | 0.959 |
|  |  | (5.47) | (5.44) | (5.03) | (0.00) | (0.00) | (0.01) | (0.00) | (0.01) | (0.00) |
|  | 4 | 20.28 | 20.46 | 23.99 | 0.856 | 0.849 | 0.831 | 0.961 | 0.962 | 0.954 |
|  |  | (5.71) | (5.7) | (5.23) | (0.02) | (0.02) | (0.01) | (0.01) | (0.01) | (0.01) |

EXAMPLES

Example 1

Analysis with Glioblastoma Biological Datasets

It is intended to combine a gene-gene network with patient's gene-expression profile into one network, coupled with some advanced technique (i.e. $L_{1/2}$). As such, the main gene interaction or key biomarkers amongst the diseases can be captured.

In this example, the KEGG signaling pathway information with a glioblastoma gene-expression dataset was used (Horvath et al. Proc. Natl. Acad. Sci. USA. 103, 2006, 17402-17407). The gene expression dataset contains the expression profiles of 22283 genes for 120 patients. Time to death was considered as the response variable. In the analysis, genes that only can be linked to the KEGG regulatory network were considered so as to identify the sub-networks of the KEGG regulatory network that are associated with glioblastoma. By integrating the gene expression data into the KEGG regulatory pathways, the final KEGG network was found to include 1418 genes and 9816 edges. 10-fold cross-validation (CV) technique was used to tune the regularization parameters, and the training error of the prediction model was reported based on the 10-fold CV.

Table 2 shows the results of the novel $L_{1/2}$ approach using the solver $$\frac{\sqrt[3]{54}}{4}(\lambda)^{\frac{2}{3}}$$

of the present invention, and $L_1$, $L_{1/2}$ approaches using a thresholding $$\frac{3}{4}(\lambda)^{\frac{2}{3}}$$

on glioblastoma dataset.

It was found that the network-constraint with novel $L_{1/2}$ approach has selected fewer numbers of genes and edges than that of the $L_1$, $L_{1/2}$ approaches using a thresholding $$\frac{3}{4}(\lambda)^{\frac{2}{3}}.$$

Further, the prediction performance of the novel $L_{1/2}$ approach also was better than the other two methods.

TABLE 2

Results obtained from using novel $L_{1/2}$ approach of the present invention, as well as $L_1$ and $L_{1/2}$ approaches, on glioblastoma biological datasets.

|  | No. of genes | No. of edges | 10-fold CV error | The common genes |
|---|---|---|---|---|
| Network with the novel $L_{1/2}$ approach | 54 | 69 | 1.623 |  |
| Network with the $L_{1/2}$ approach | 63 | 64 | 1.729 | 9* |
| Network with the $L_1$ approach | 90 | 95 | 1.921 |  |

Figure 3:
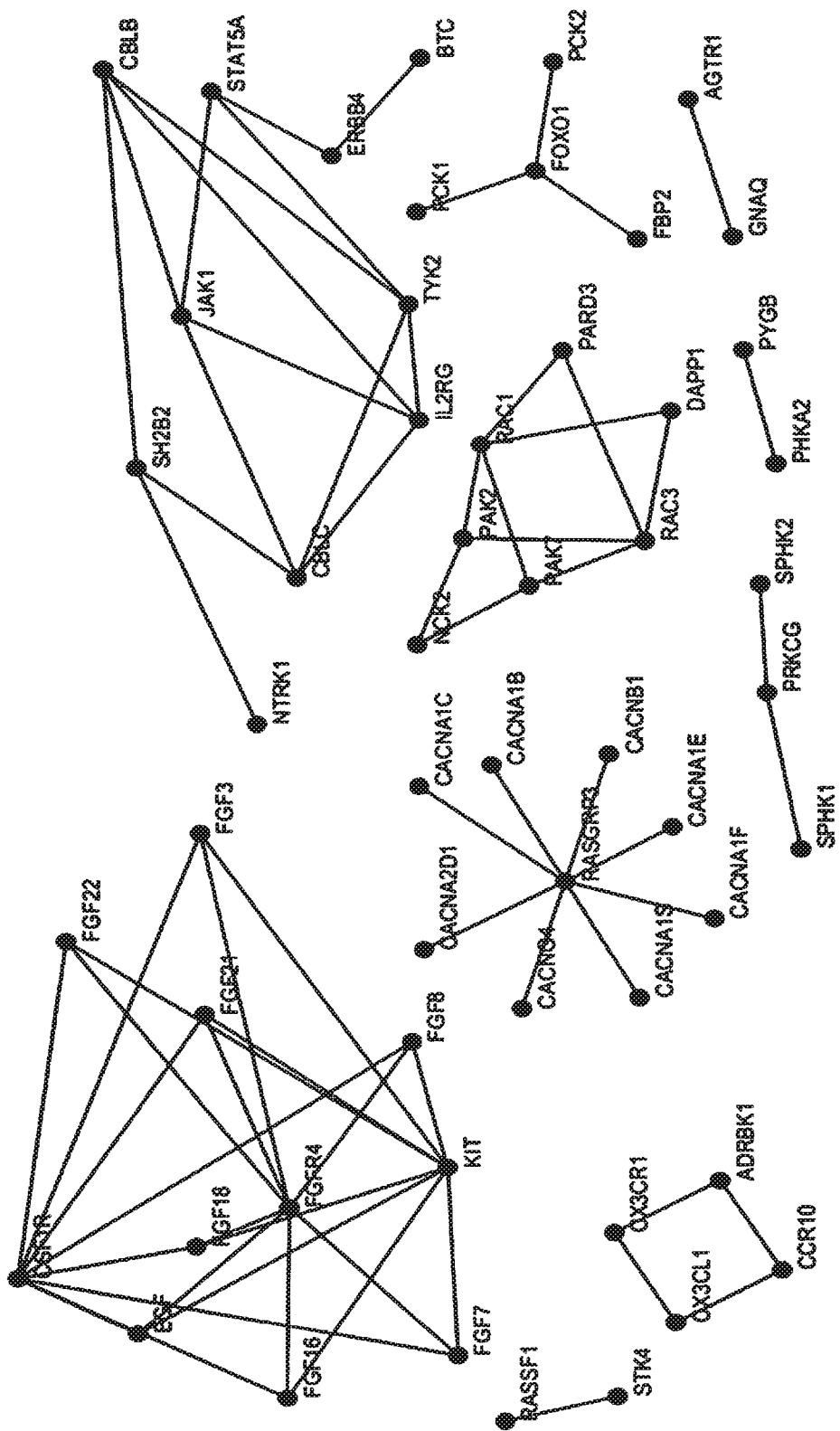
FIG. 3 shows the associations of various genes with glioblastoma determined from a system of the present invention, in which a thresholding representation of $$\frac{\sqrt[3]{54}}{4}(\lambda)^{\frac{2}{3}}$$

FIG. 3 shows the associations of various genes with glioblastoma determined from a system of the present invention, in particular it shows the sub-networks identified by network-constraint with the novel $L_{1/2}$ penalty procedure of the system of the present invention. From literature surveys, several pathways were found to be associated with glioblastoma. Based on the experimental results obtained in this example, there are over seven potential targets genes for glioblastoma.

The largest sub-network determined includes genes participating in the PI3K-AKT signaling pathway, namely genes FGFR4, FGF16, EGF, FGF3, FGF7, FGF8, FGF21, FGF22, FGF18, CSF1R, and KIT etc. Without limited by theory, it is believed that the PI3K/AKT signaling pathway regulates glioma cell proliferation. Studies have shown that inhibition of Akt significantly increased the survival of tumor-bearing mice and nearly a fourth of the mice remained in remission four months after the treatment period. It is believed that the PI3K/AKT signaling pathway is a viable therapeutic target for glioma treatment.

The second sub-network determined includes genes participating in the JAK-STAT signaling pathway, namely genes CBLC, CBLB, IL2RG, STAT5A, TYK2, JAK1, NTRK1, and ERBB4 etc. Studies show that the JAK/STAT pathway may play important role in the progression of human gliomas. The activated state of this pathway might be a potent tool for predicting the clinical prognosis of patients with glioma.

The third sub-network determined includes genes participating in the MAPK signaling pathway, namely genes RASGRP3, CACNG4, CACNA1B, CACNA1C, CACNA1E, CACNA1F, CACNA1S, CACNA2D1, and CACNB1 etc. Studies show that the prognostic relevance of MAPK expression in glioblastoma multiforme and the expression was significantly correlated with survival time.

The targeted genes include sphingosine kinase type 1 (SphK1) which may be important for proliferation of glioma cells, as pharmacological inhibition or down-regulation of its expression significantly decreased cell growth by preventing cells from exiting the G1 phase of the cell cycle and SphK1 should be considered as a new therapeutic target for glioblastoma.

FOXO1 is an important TF involved in the regulation of a range of critical processes in mammalian cells, including proliferation, differentiation, apoptosis, metabolism and responses to oxidative stress and DNA damage (Accili, D. and Arden, K. C. Cell. 117, 2004, 421-426). It might contribute to the risk of death from glioblastoma.

Fibroblast growth factors receptor 4 (FGFR4) significantly reduced in vitro cell growth and clonogenicity in the tested glioma cell models and it is suggested that FGFR4 can be a potential target for therapeutic interventions.

V-kit Hardy-Zuckerman 4 feline sarcoma viral oncogene homolog (KIT) is also reported to be frequently involved in tumourigenic processes and constitutes an attractive therapeutic target for glioblastoma.

ErbB4, the fourth member of the EGFR family has both oncogenic and tumor suppressive activity dependent upon isoform expression. Due to a potential angiogenic role of ErbB4 in glioma and reduced patient survival times following ErbB4 activation, ErbB4 may be a new therapeutic target in glioma.

It is suggested that Rho family small GTPases are key signaling elements that control the malignant behavior of cancer cells. Especially, Chan (Chan, A. Y., et al. Oncogene. 24, 2005, 7821-7829) showed a functional analysis of Rac1 and Rac3 using RNA interference, revealed a critical role for these GTPases in the invasive behavior of glioma and breast carcinoma cells. Targeting rac1 or RhoG-mediated signaling presents a possible avenue for glioblastoma therapy.

FIGS. 4 and 5 show associations of various genes with glioblastoma determined from a system using solver $L_{1/2}$ and $L_1$ penalty procedures, in which a thresholding representation of $$\frac{3}{4}(\lambda)^{\frac{2}{3}}$$

was applied. Based on the results, the novel solver $L_{1/2}$ outperformed these two methods. For example, the number of selected genes and edges of $L_1$ penalized procedure are much more than that of the $L_{1/2}$ method applied in the system of the present invention.

Moreover, according to literature surveys, there are only six potential targets genes for glioblastoma therapy and fewer pathways associated with glioblastoma were determined based on the results. The same observation can also be found by using the system of the present invention, in which a thresholding representation of $$\frac{\sqrt[3]{54}}{4}(\lambda)^{\frac{2}{3}}$$

was applied.

Example 2

Analysis with AML and Lung Cancer Biological Datasets

Further experiments were conducted to verify the performance of the network-constraint with novel solver $L_{1/2}$ penalty procedures. Two gene-expression databases were used, namely acute myeloid leukemia (AML) dataset and lung cancer dataset. Similar to Example 1, each of these datasets was incorporated with KEGG pathways respectively.

The AML dataset was obtained from Bullinger et al. (Bullinger, L. et al. N. Engl. J. Med. 250, 2004, 1605-161). It contains the expression profiles of 6283 genes for 116 patients. Among them, 354 genes can be found in the KEGG network having 35 pathways.

The lung cancer dataset is obtained from Beer et al. (Beer, D. G., et al. Nat. Med. 8, 2002, 816-824). It consists of gene expressions of 4966 genes for 83 patients. Among them, 935 genes can be found in the KEGG network having 35 pathways.

Table 3 shows the results obtained by each approach on the AML and lung cancer datasets. The numbers of genes and edges selected by the novel solver $L_{1/2}$ penalized method are significantly less than that of the other two penalized methods. Particularly, the number of potential targets genes selected by the novel solver $L_{1/2}$ penalized method for AML and lung cancer therapy are comparable or even more than that of the other two penalized methods.

TABLE 3

Results obtained from using novel $L_{1/2}$ approach of the present invention, as well as $L_1$ and $L_{1/2}$ approaches, on AML and lung cancer biological datasets.

| Dataset | No. of genes | | | No. of edges | | | 10-fold CV error | | | No. of targets* | | |
|---|---|---|---|---|---|---|---|---|---|---|---|---|
| | Novel $L_{1/2}$ | $L_{1/2}$ | $L_1$ | Novel $L_{1/2}$ | $L_{1/2}$ | $L_1$ | Novel $L_{1/2}$ | $L_{1/2}$ | $L_1$ | Novel $L_{1/2}$ | $L_{1/2}$ | $L_1$ |
| AML | 55 | 59 | 90 | 34 | 37 | 55 | 2.331 | 2.369 | 2.51 | 6 | 6 | 3 |
| Lung cancer | 83 | 87 | 92 | 52 | 61 | 69 | 1.963 | 1.988 | 2.023 | 9 | 7 | 7 |

The system and method of the present invention is particular advantageous for molecular researches, e.g. cancer studies. The method combines biological pathways information with gene-expression data can be used to identifying new targets for drug design and targeted drug therapy. Also, this method is also capable of determining the correlation between biological features and a medical condition. The system and the method of the present invention can attain higher prediction accuracy than that the existing approaches with fewer but informative pathways.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include standalone computers, network computers and dedicated hardware devices. Where the terms "computing system" and "computing device" are used, these terms are intended to cover any appropriate arrangement of computer hardware capable of implementing the function described.

It will be appreciated by persons skilled in the art that the term "database" may include any form of organized or unorganized data storage devices implemented in either software, hardware or a combination of both which are able to implement the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A method of determining at least one biological feature associated with cancer, comprising the steps of:
    processing, using one or more processors, at least some biological data in a dataset using a regression model to determine and/or optimize parameters in the regression model thereby solving the regression model, the biological data being related to a plurality of samples from humans at least some of which have the cancer, each of the plurality of samples including a plurality of biological features, each of the biological features being at least one of presence of a gene, gene expression, presence of a gene product or amount of a gene product; and
    processing, using one or more processors, the biological data using the solved regression model with a biological model to determine one or more biological features that are associated with the cancer,
    wherein the solved regression model includes $L_{1/2}$ penalized network-constrained regression defined by:

$$L(\lambda_1, \lambda_2, \beta) = L(\gamma, \beta^*) = (y^* - X^*\beta^*)^T(y^* - X^*\beta^*) + \sum_{j=1}^{p} |\beta_j^*|^{1/2}$$

where $L = U\Gamma U^T$ and $S = U\Gamma^{1/2}$, $\gamma = \lambda_1/\sqrt{1+\lambda_2}$, $\beta^* = \sqrt{1+\lambda_2}\,\beta$, and $X^*_{(n+p)\times p} = (1+\lambda_2)^{-1/2}\begin{pmatrix} X \\ \sqrt{\lambda_2}\,S^T \end{pmatrix}$, $Y^*_{(n+p)} = \begin{pmatrix} Y \\ 0 \end{pmatrix}$, and where L is a function of the solved regression model, y is a corresponding dependent variable, X is a matrix of biological features measured from the samples, γ and β are parameters to be determined and/or optimized, $\lambda_1$ and $\lambda_2$ are regularization parameters, n is a total number of the samples, p is a total number of biological features, S is a parameter to be determined, U and Γ are determined from L using matrix factorization; and T is a matrix transpose symbol.

2. The method in accordance with claim 1, wherein the biological model includes biological network information associated with the cancer and the biological features.

3. The method in accordance with claim 2, wherein the biological network information is arranged to represent a biological process, a molecular interaction and/or a reaction network associated with the biological features.

4. The method in accordance with claim 2, wherein the step of processing the biological data using the solved regression model with the biological model comprises a step of integrating the biological network information into the biological data by using a graph Laplacian constraint approach.

5. The method in accordance with claim 4, wherein the graph Laplacian constraint approach regularizes the biological network information and includes an iterative transformation to obtain at least one estimation representing association of the biological features with the cancer.

6. The method in accordance with claim 5, wherein the iterative transformation includes an univariate half thresholding operation of a coordinate descent optimization of the regularized biological network information.

7. The method in accordance with claim 6, wherein a thresholding representation of $$\frac{\sqrt[3]{54}}{4}(\lambda)^{\frac{2}{3}}$$

is used in the univariate half thresholding operation, wherein λ denotes the regularization parameter $\lambda_1$.

8. The method in accordance with claim 1, wherein the biological features associated with the cancer include one or more biomarker and/or indicator arranged to represent an indication of the cancer.

9. A system for determining at least one biological feature associated with cancer, comprising one or more processors arranged to:
    process at least some biological data in a dataset using a regression model to determine and/or optimize parameters in the regression model thereby solving the regression model, the biological data being related to a plurality of samples from humans at least some of which have the cancer, each of the plurality of samples having a plurality of biological features, each of the biological features being at least one of presence of a gene, gene expression, presence of a gene product or amount of a gene product; and process the biological data using the solved regression model with a biological model to determine one or more biological features that are associated with the cancer, wherein the solved regression model includes $L_{1/2}$ penalized network-constrained regression defined by:

$$L(\lambda_1, \lambda_2, \beta) = L(\gamma, \beta^*) = (y^* - X^*\beta^*)^T(y^* - X^*\beta^*) + \sum_{j=1}^{p} |\beta_j^*|^{1/2}$$

where $L = U\Gamma U^T$ and $S = U\Gamma^{1/2}$, $\gamma = \lambda_1 / \sqrt{1+\lambda_2}$, $\beta^* = \sqrt{1+\lambda_2}\,\beta$, and $X^*_{(n+p)\times p} = (1+\lambda_2)^{-1/2} \begin{pmatrix} X \\ \sqrt{\lambda_2}\, S^T \end{pmatrix}$, $Y^*_{(n+p)} = \begin{pmatrix} Y \\ 0 \end{pmatrix}$, and where L is a function of the solved regression model, y is a corresponding dependent variable, X is a matrix of biological features measured from the samples, γ and β are parameters to be determined and/or optimized, $\lambda_1$ and $\lambda_2$ are regularization parameters, n is a total number of the samples, p is a total number of biological features, S is a parameter to be determined, U and Γ are determined from L using matrix factorization; and T is a matrix transpose symbol.

10. The system in accordance with claim 9, wherein the biological model includes biological network information associated with the cancer and the biological features.

11. The system in accordance with claim 10, wherein the one or more processors is further arranged to integrate the biological network information into the biological data via a graph Laplacian constraint approach.

12. The system in accordance with claim 11, wherein the graph Laplacian constraint approach regularizes the biological network information and includes an iterative transformation for obtaining at least one estimation representing association of the biological features with the cancer.

13. The system in accordance with claim 12, wherein the iterative transformation includes an univariate half thresholding operation of a coordinate descent optimization of the regularized biological network information.

14. The system in accordance with claim 9, wherein the biological features associated with the cancer includes one or more biomarker and/or indicator arranged to represent an indication of the cancer.

* * * * *